United States Patent
Alexiades-Armenakas

(10) Patent No.: US 8,529,925 B2
(45) Date of Patent: Sep. 10, 2013

(54) MULTI-ACTIVE MICROTARGETED ANTI-AGING SKIN CARE CREAM POLYMER TECHNOLOGY

(71) Applicant: NY Derm LLC, New York, NY (US)

(72) Inventor: Macrene Alexiades-Armenakas, New York, NY (US)

(73) Assignee: NY Derm, LLC, New York, NY (US)

( * ) Notice: Subject to any disclaimer, the term of this patent is extended or adjusted under 35 U.S.C. 154(b) by 0 days.

(21) Appl. No.: 13/663,908

(22) Filed: Oct. 30, 2012

(65) Prior Publication Data

US 2013/0078294 A1  Mar. 28, 2013

Related U.S. Application Data

(62) Division of application No. 13/154,844, filed on Jun. 7, 2011.

(60) Provisional application No. 61/352,956, filed on Jun. 9, 2010.

(51) Int. Cl.
*A61K 8/02* (2006.01)
*A61K 8/00* (2006.01)
*A01N 65/00* (2009.01)

(52) U.S. Cl.
USPC ............ 424/401; 424/195.15; 424/59

(58) Field of Classification Search
USPC ............... 424/401, 59, 195.15
See application file for complete search history.

(56) References Cited

U.S. PATENT DOCUMENTS 6,083,529 A * 7/2000 Manzo et al. ............ 424/450
2006/0222695 A1* 10/2006 Zadini et al. ............ 424/450

FOREIGN PATENT DOCUMENTS

WO  WO 2009/127058 A1 * 10/2009

* cited by examiner

*Primary Examiner* — Aradhana Sasan
(74) *Attorney, Agent, or Firm* — Charles D. Gunter, Jr.

(57) ABSTRACT

A comprehensive, single agent cosmetic cream or lotion containing a high number of ingredients that target anti-aging in a defined manner. The cream or lotion contains a high number and variety of active substances that demonstrate excellent safety and efficacy in all of the various defined categories of skin aging, including but not limited to wrinkles, abnormal pigment or brown spots due to aging of the skin and an unexpectedly high efficacy in the reduction of redness and acne and rosacea blemishes.

11 Claims, 3 Drawing Sheets

Comprehensive Grading Scale for Assessment of Rhytides, Laxity and Photodamage.

| Grading Scale | Descriptive Parameter | Categories of Skin Aging and Photodamage ||||||| 
| | | Rhytides | Laxity | Elastosis | Dyschromia | Erythema-Telangiectasia (E-T) | Keratoses | Texture |
|---|---|---|---|---|---|---|---|---|
| 0 | none | none | none | none | none | none | none | none |
| 1 | mild | wrinkles in motion, few superficial | localized to nasolabial (nl) folds | early, minimal yellow hue | few (1-3) discrete small (<5mm) lentigines | pink E or few T, localized to single site | few | subtle irregularity |
| 1.5 | mild | wrinkles in motion, few superficial | localized nl and early melolabial l, (ml) folds | yellow hue or early, localized periorbital (po) elastotic beads (eb) | several (3-6), discrete small lentigines | fpine E or several T localized 2 sites | several | mild irregularity in few areas |
| 2 | moderate | wrinkles at rest, few, localized, superficial | localized nl/ml folds, early jowels, early submental/submandibular (sm) | yellow hue, localized po eb | multiple (7-10), small lentigines | red E or multiple T, localized to 2 sites | multiple, small | rough in few, localized sites |
| 2.5 | moderate | wrinkles at rest, multiple, localized, superficial | localized prominent nl/ml folds, jowels and sm | yellow hue, po and malar eb | multiple, small and few large lentigines | red E or multiple T, localized to 3 sites | multiple, large | rough in several, localized areas |
| 3 | advanced | wrinkles at rest, multiple, forehead, periorbital and perioral sites, superficial | prominent nl/ml folds, jowels and sm, early neck strands | yellow hue, eb involving po, malar and other sites | many (10-20) small and large lentigines | violaceous E or many T, multiple sites | many | rough in multiple, localized sites |
| 3.5 | advanced | wrinkles at rest, multiple, forehead, periorbital and perioral sites, superficial | deep nl/ml folds, prominent jowels and sm, prominent neck strands | deep yellow hue, extensive eb with little uninvolved skin | Numerous (>20) or multiple large with little uninvolved skin | deep, violaceous E, numerous T throughout | little uninvolved skin | mostly rough, little uninvolved skin |
| 4 | severe | wrinkles throughout, numerous, extensively distributed, deep | marked nl/ml folds, jowels and sm, neck redundancy and strands | deep yellow hue, eb throughout comedones | numerous, extensive, no uninvolved skin | deep, violaceous E, numerous T throughout | no uninvolved skin | rough throughout |

Fig. 1

EVALUATION OF SKIN IRRITATION

| SUBJECT NO. | BASELINE | 4 WEEKS | 6 WEEKS | 8 WEEKS |
|---|---|---|---|---|
| 1 | 0 | 0 | 0 | 0 |
| 2 | 0 | 0 | 0 | 0 |
| 3 | 0 | 0 | 0 | 0 |
| 4 | 0 | 0 | 0 | 0 |
| 5 | 0 | 0 | 0 | 0 |
| 6 | 0 | 0 | 0 | 0 |
| 7 | 0 | 0 | 0 | 0 |
| 8 | 0 | 0 | 0 | 0 |
| 9 | 0 | 0 | 0 | 0 |
| 10 | 0 | 0 | 0 | 0 |
| 11 | 0 | 0 | 0 | 0 |
| 12 | 0 | 0 | 0 | 0 |
| 13 | 0 | 0 | 0 | 0 |
| 14 | 0 | 0 | 0 | 0 |
| 15 | 0 | 0 | 0 | 0 |
| 16 | 0 | 0 | 0 | 0 |
| 17 | 0 | 0 | 0 | 0 |
| 18 | 0 | 0 | 0 | 0 |
| 19 | 0 | 0 | 0 | 0 |
| 20 | 0 | 0 | 0 | 0 |
| 21 | Discontinued | | | |
| 22 | 0 | 0 | 0 | 0 |
| 23 | 0 | 0 | 0 | 0 |
| 24 | 0 | 0 | 0 | 0 |
| 25 | 0 | 0 | 0 | 0 |
| 26 | 0 | 0 | 0 | 0 |
| 27 | 0 | 0 | 0 | 0 |
| 28 | 0 | 0 | 0 | 0 |
| 29 | 0 | 0 | 0 | 0 |
| 30 | 0 | 0 | 0 | 0 |
| 31 | 0 | 0 | 0 | 0 |
| 32 | 0 | 0 | 0 | 0 |
| MEAN | 0.0 | 0.0 | 0.0 | 0.0 |

Scale for Scoring Skin Irritation
0 = No evidence of any irritation
+ = Barely perceptible irritation present
1 = Mild irritation present
2 = Moderate irritation present
3 = Marked irritation present
4 = Severe irritation present

Fig. 2

EVALUATION OF CROW'S FEET FINE LINES/WRINKLES

| SUBJECT NO. | BASELINE | 4 WEEKS | 6 WEEKS | 8 WEEKS |
|---|---|---|---|---|
| 1 | 5 | 5 | 5 | 5 |
| 2 | 5 | 5 | 5 | 5 |
| 3 | 7 | 6 | 4 | 6 |
| 4 | 6 | 5 | 5 | 6 |
| 5 | 6 | 5 | 5 | 5 |
| 6 | 5 | 5 | 5 | 7 |
| 7 | 6 | 6 | 5 | 6 |
| 8 | 5 | 5 | 5 | 5 |
| 9 | 6 | 5 | 5 | 4 |
| 10 | 7 | 6 | 6 | 5 |
| 11 | 5 | 5 | 5 | 5 |
| 12 | 6 | 6 | 5 | 5 |
| 13 | 5 | 5 | 4 | 5 |
| 14 | 6 | 5 | 4 | 4 |
| 15 | 5 | 5 | 4 | 4 |
| 16 | 6 | 5 | 5 | 4 |
| 17 | 6 | 5 | 5 | 4 |
| 18 | 6 | 6 | 5 | 5 |
| 19 | 6 | 6 | 5 | 5 |
| 20 | 7 | 6 | 6 | 5 |
| 21 | Discontinued | | | |
| 22 | 6 | 6 | 6 | 6 |
| 23 | 6 | 5 | 5 | 5 |
| 24 | 7 | 7 | 6 | 5 |
| 25 | 7 | 6 | 5 | 4 |
| 26 | 6 | 5 | 5 | 5 |
| 27 | 6 | 5 | 5 | 5 |
| 28 | 5 | 5 | 5 | 4 |
| 29 | 6 | 5 | 4 | 5 |
| 30 | 6 | 5 | 5 | 5 |
| 31 | 6 | 6 | 4 | 5 |
| 32 | 7 | 6 | 4 | 4 |
| MEAN | 5.9 | 5.4 | 4.9 | 4.9 |

Scoring Scale for Crow's Feet Fine Lines/Wrinkles
 0 = None
 1 - 3 = Slight
 4 - 6 = Noticeable
 7 - 9 = Very Noticeable

Fig. 3

MULTI-ACTIVE MICROTARGETED ANTI-AGING SKIN CARE CREAM POLYMER TECHNOLOGY

CROSS-REFERENCE TO RELATED APPLICATION

This application is a division of Ser. No. 13/154,844, filed Jun. 7, 2011, which claimed priority from a previously filed provisional application Ser. No. 61/352,956, filed Jun. 9, 2010, entitled "Multi-Active Microtargeted Anti-Aging Skin Cream Polymer Technology," by the same inventor.

BACKGROUND OF THE INVENTION

1. Field of the Invention

The present invention relates to a comprehensive multi-active anti-aging and skin rejuvenation cream and lotion especially beneficial for the various categories of skin aging, including but not limited to wrinkles, redness and abnormal pigment or brown spots and is associated with an unexpected result in the dramatic reduction of redness, acne and rosacea.

2. Description of the Prior Art

The need for anti-aging creams/lotions and moisturizers without a prescription is evident. Topical tretinoin cream has been shown to reduce wrinkles but has a high incidence of side effects and requires a prescription. Alpha-hydroxy acids have been reported to increase the risk of sunburn and are also irritating to sensitive skin types. Over-the-counter skin care preparations are generally inadequate in providing anti-aging results, and often make the skin feel greasy and exacerbate acne, as they often include petrolatum or mineral oil. Their moisturizing qualities also tend to vanish quickly, and they tend to yield little, if any, results in the aforementioned categories of skin aging. In addition, many include potentially toxic parabens, propylene glycol and fragrances, which are irritants. Prior scientific research has shown the efficacy of small combinations of few active substances to target a specific category of skin aging, but the comprehensive combination of multiple classes of active substances systematically targeting the various categories of aging has not been carried out.

Finally, the plethora of anti-aging skin products on the market which contain very few ingredients demonstrated in the published literature to provide clinical results to the skin has resulted in confusion in the market among consumers and skin care providers alike. A dire need for a comprehensive, inclusive anti-aging skin care agent that provides a large number and variety of anti-aging ingredients shown to provide safety and efficacy in addressing the various categories of skin aging is addressed by the current invention.

U.S. Pat. No. 5,153,230 was issued to Jaffery on Oct. 6, 1992 and discloses a topical skin cream composition designed to prevent and treat aging skin. The active ingredient is glycolic acid in concentrations up to 3.5 percent by weight. The composition alternatively may include vitamin A palmitate and/or vitamin E acetate. Preservatives are included in the composition to increase shelf life. Other ingredients may be included in the composition but no natural ingredients such as coffee seed extract, yerba mate tea extract, feverfew extract or mushroom extract are included in the composition. Additionally, glycolic acid when used regularly is irritating to sensitive skin, and photosensitizing, increasing the risk of sunburn.

U.S. Pat. No. 5,254,331 issued to Mausner on Oct. 19, 1993 describes a skin cream composition designed to minimize environmental stress on the skin, improve firmness and elasticity, and counteract dryness. The appearance of wrinkles is prevented, delayed, or corrected. The skin cream of Mausner contains a protein complex with serum proteins and hydrolyzed animal proteins; a protein-amino acid-vitamin-nucleotide complex with propylene glycol, serum proteins, niacinamide, water, adenosine phosphate, and arginine; and a dimethylsilanyl hyaluronate complex. However, the skin cream of Mausner is lacking plant-derived polyphenols and antioxidants, and contains the undesirable propylene glycol and animal- or human-derived ingredients (serum proteins).

U.S. Pat. No. 5,391,373 issued to Mausner on Feb. 21, 1995 discloses a skin cream composition which provides retexturization, produces smoothness, minimizes age spots, improves color, and increases firmness and moisture content of the skin. The composition comprises sodium lactate; a micellar complex comprising horse chestnut extract, *Crataegus* extract, water, panthenol, propylene glycol, phospholipids, phenoxyethanol, glycosphingolipids, chlorphenesin, and cholesterol; a protein complex comprising serum proteins, hydrolyzed animal proteins, and glycogen; a carbohydrate-based complex comprising dextran, glycine, and glucosamine; a long-chain fatty acid ester of retinol; a long-chain fatty acid ester of ascorbic acid; and a short-chain fatty acid ester of tocopherol. Other cosmetic components may be included. This composition by Mausner contains retinol, which is an irritant to many users, propylene glycol, which has been reported to result in untoward effects and potential toxicity and animal- or human-derived agents, such as serum proteins. In addition, the composition lacks DNA repair, peptides and most classes of plant-derived polyphenols.

U.S. Pat. No. 5,571,503 issued to Mausner on Nov. 5, 1996 describes a cosmetic composition which provides protection against moisture loss and damage due to free radical activity and ultraviolet light. The composition contains an complex with propylene glycol, hydrolyzed wheat protein, mannitol, glycogen, yeast extract, ginseng extract, linden extract, calcium pantothenate, horse chestnut extract, and biotin; a micellar complex with phospholipids, glycosphingolipids, panthenol, *Crataegus* extract, cholesterol, and sodium hyaluronate; an anti-free radical complex with melanin, a short-chain fatty acid ester of tocopherol, a long-chain fatty acid ester of retinol, and a long-chain fatty acid ester of ascorbic acid; and a sun screen. Other cosmetic components may be included. However, the composition is lacking in amino acids, DNA repair, peptides and polyphenols, and conversely contains propylene glycol, which is sensitizing and retinol, which has a high incidence of imitation to sensitive skin types.

U.S. Pat. No. 5,658,580 issued to Mausner on Aug. 19, 1997 describes a skin cream composition which provides retexturization and smoothening of the skin, minimization of age spots, improvement of skin color, increase in skin firmness and moisturization to the skin. The skin cream composition contains sodium lactate; a long-chain fatty acid ester of ascorbic acid; a short-chain carboxylic acid ester of tocopherol; witch hazel; and horsetail extract. The composition lacks the numerous polyphenols, anti-oxidants, DNA repair and peptide classes.

U.S. Pat. No. 6,989,150 issued to Golz-Berner on Jan. 24, 2006 describes a cosmetic preparation of active substances which protects the skin against free radical damage. The composition contains bark extract of quebracho blancho containing proanthocyanidine oligomers, a silkworm extract with cecropine, amino acids and a vitamin mixture, phospholipids (which are misspelled in the patent), yeast product and cyclodextrines. Alternatively, it contains plant extracts from acerola, sea weed, citrus, bitter orange, cherry, papaya, tea, coffee beans, skin tree and angelica. The composition is claimed as a radical protection factor, but not described with respect to anti-aging and does not contain *Ilex paraguariensis*, peptides, DNA repair, plankton or algae extracts, resveratrol or other actives described herein which target the multiple categories of anti-aging.

U.S. Pat. No. 6,426,080 issued to Golz-Berner on Jul. 30, 2002 describes a cosmetic preparation of active substances that protects the skin from free radical damage. The composition contains *Quebraco blanco* bark extract, silkworm extract, amino acids, a vitamin mixture, phospholipids, and a cationic or anionic hydrogel. It may also contain plant extracts from acerola, sea weed, citrus, bitter orange, papaya, tea, coffee beans, *Mimosa tenuiflora* and angelica. The composition is described for use in protection against free radicals and does not contain peptides, *Ilex paraguensis* extract, DNA repair molecules, resveratrol or other actives targeting the multiple categories of aging of the skin.

U.S. Pat. No. 6,270,780 issued to Carson on Aug. 7, 2001 describes a cosmetic composition containing resveratrol. The composition contains resveratrol and may be combined with an alpha-hydroxy acid. The composition is claimed to improve or prevent wrinkled, dry, aged or photodamaged skin and to improve skin thickness, elasticity, flexibility, radiance, glow and plumpness. It is also claimed to lighten skin color and control skin irritation or inflammation. The composition does not include any other active substances except alpha hydroxy acid, which may be an irritant.

U.S. Pat. No. 6,358,517 issued to Pillai on Mar. 19, 2002 describes a cosmetic composition containing resveratrol and retinoids. The composition is claimed to improve or prevent wrinkled, dry, aged or photodamaged skin and to improve skin thickness, elasticity, flexibility, radiance, glow and plumpness. The composition does not include other active substances described herein for the treatment of aging of the skin.

U.S. Pat. No. 6,680,062 issued to Miuzzuddin on Jan. 20, 2004 describes a composition containing salicylic acid, a phytosphingosine, green tea, hinoitiol, *gorgoinian* extract, and polysaccharide. The composition is described to provide a method for decreasing irritation on the skin caused by rosacea and for treating the telangiectatic symptom of rosacea. The composition does not include *Ilex paraguariensis* extract, *Coffea arabica* extract, *Theobroma cacao* extract, *Chrysanthemum parthenum* extract or bisabolol, contained in the current invention and which provide the unexpected extensive redness-relieving benefits described herein. In addition, the composition does not include *Hordeum distichon* (Barley) extract, which contains EDG-like molecules, and provides the unexpected acne and rosacea treatment benefits described herein.

The patents, referenced herein, are notable for the inclusion of a limited number of actives that are neither ordered nor classified according to their anti-aging properties, nor rationally selected to comprehensively target all categories of skin aging. The patents do not define the various categories of skin aging nor do they rigorously define the various categories of actives with respect to clinical outcome. The patents referenced herein do not comprehensively include a variety and range of actives rationally selected based upon proven safety and efficacy and systematic targeting of all categories of skin aging. In addition, none of the prior art included *Ilex paraguensis* extract in skin cream compositions heretofore described. The patents do not disclose the same topical cream and lotion compositions as those of the present invention.

The skin rejuvenation cream and lotion of the present invention is better able to reverse and target the various categories of skin aging and rejuvenate the skin. The skin rejuvenation cream and lotion compositions of the present invention are specifically designed to classify anti-aging ingredients according to anti-aging category targeted, and systematically target the various categories of skin aging by moisturizing and improving wrinkles, inducing DNA and cellular repair, providing barrier repair, reversing UV induced damage, reducing redness and decreasing abnormal pigment deposition. Furthermore, the current invention systematically targets numerous individual molecules to desired locations within the skin using multiple liposomal technologies. Finally, the current invention afforded the unexpected results of dramatic improvement in redness, acne and rosacea.

None of the above inventions and patents, taken either singly or in combination, is seen to describe the instant invention as claimed.

SUMMARY OF THE INVENTION

The present invention has its genesis in the recognition of various specific categories of skin aging and photodamage, which have previously been defined and published by the inventor. The multi-active microtargeted anti-aging skin cream composition and skin cream polymer technology of the invention, for the first time systematically targets each of these categories of skin aging and photodamage in a single cosmetic cream or lotion product. The active ingredients in the formulations of the invention are specifically selected and designed to target a protocol of skin aging in a way that was not appreciated in the prior art.

The anti-aging and skin rejuvenation cream and lotion compositions of the current invention include a unique composition with DNA repair molecules, polyphenols from a variety of plant sources, amino acids, hyaluronic acid in small molecular weights, antioxidants of all classes, UV repair molecules of all classes, peptides and rich emollients that are combined actively to reduce wrinkles, reverse sun damage, diminish redness and abnormal pigment, and improve the signs in the various categories of skin aging. The present invention is to be applied daily on the skin to obtain results in reducing wrinkles, redness and abnormal discolorations that result from UV damage and aging. The present invention also yields the unexpected finding of dramatic reduction in redness and improvement in acne and rosacea. The composition includes:

Ingredient List.
Water (Aqua)
Dimethicone
Glycerin
*Helianthus annuus* (Sunflower) Seed Oil Unsaponifiables
Stearic Acid
Sorbitan Stearate
Ferulic Acid
Hydroxyethylcellulose
Lecithin
Sodium Hyaluronate
*Tremella fuciformis* Polysaccharide (Mushroom extract)
*Coffea arabica* (Coffee) Seed Extract*
*Theobroma cacao* (Cocoa) Seed Butter*
*Helianthus annuus* (Sunflower) Seed Oil*
*Chrysanthemum parthenium* (Feverfew) Extract*
Bisaholol (Active component of Chamomile)
Hydrogenated Soy Lecithin
*Arabidopsis thaliana* Extract
*Ilex paraguariensis* (Yerba mate) Leaf Extract*
Hydrolyzed Vegetable Protein
Laurdimonium Hydroxypropyl Hydrolyzed Soy Protein
Caffeine Tetrahexyldecyl Ascorbate
Resveratrol
Acetyl Tetrapeptide-2
Dextran
Magnesium Ascorbyl Phosphate
Tocopherol
Xanthan Gum
Ergothioneine
Ethylhexylglycerin
Cetyl Alcohol
Trimethylolpropane Tricaprylate/Tricaprate
Sodium PCA
Sodium Lactate
Arginine
Aspartic Acid
PCA
Glycine
Alanine
Serine
Valine
Proline
Threonine
Isoleucine
Histidine
Phenylalanine
Acetyl Tyrosine
Squalane
Sodium Methyl Stearoyl Taurate
Adenosine Triphosphate
Sodium Hydroxide
hydroxypropylmethylcellulose Stearoxy Ether
Alcohol
Disodium EDTA
Butylene Glycol
Caprylyl Glycol
Ethylhexylglycerin
Hexylene Glycol
Phenoxyethanol
Alternatively, may also include:
*Simmondsia chinensis* (Jojoba) butter
Sorbitan stearate
*Santalum album* (Sandalwood) Extract
*Phellodendron amurense* (Bark) Extract
Hordeum distichon (Barley) Extract
Hydrogenated coco glycerides
*Theobroma cacao* (Cocoa) seed butter
Micrococcus lysate
Plankton and Blue Algae Extract
Palmitoyl Oligopeptide
Palmitoyl Tetrapeptide-7
Carbomer
*USDA Certified Organically Grown
Paraben-free
Fragrance-free
Propylene glycol-free
No animal testing or animal-derived ingredients
Made in USA from ingredients sourced in the USA The multi-active microtargeted anti-aging skin cream polymer technology of the invention also includes a skin care protocol which includes the steps of
presenting a patient for examination;
applying an anti-aging cream or lotion to the face of the patient;
comparing the patient's resultant skin quality to the list of previously defined anti-aging categories;
targeting a comprehensive skin care regimen for the patient based upon the comparison with the list of previously defined anti-aging categories, the resulting skin care regimen containing anti-aging actives which are categorized according to the aging categories they address; and
wherein the categories of actives are defined to include at least DNA repair, cellular repair, anti-wrinkle, anti-redness, anti-pigment, anti-UV damage, barrier repair, emollient/moisturizer characteristics, improved skin texture and UV damage reversal.

The targeted series of anti-aging actives as defined by the previous protocol, are all preferably contained in a single cosmetic product formulation. In its most preferred form, the patient treatment defined by the previously described protocol includes a variety and range of actives rationally selected based upon proven safety and efficacy and systematic targeting of all categories of skin aging.

The single cosmetic product formulation of the invention systematically targets numerous individual molecules to desired locations within the skin using multiple liposomal technologies. The single cosmetic product formulation of the invention includes numerous ingredients that are micro-encapsulated such that they are protected from surrounding ingredients and penetrate to desired strata within the skin.

The preferred single cosmetic product formulation includes as one ingredient an extract of the plant *Ilex paraguensis*.

Accordingly, it is a principal object of the invention to provide topical cream and lotion compositions for applying to the skin to comprehensively address all categories of skin aging with actives encompassing all categories of anti-aging activity, including reducing the appearance of wrinkles, laxity, redness, brown discoloration, elastosis, UV damage, poor texture, and abnormal skin growths.

It is another object of the invention to develop a pleasant feeling skin moisturizer.

It is a further object of the invention to provide topical skin cream and lotion compositions that reduce the signs of aging.

Still another object of the invention is to provide a topical skin cream and lotion composition that leaves the skin feeling soft to the touch without exacerbating acne.

It is an object of the invention to provide improved components and arrangements thereof in a topical composition for the purposes described which combines a high number and variety of anti-aging actives in a single formulation that is dependable and fully effective in accomplishing its intended purposes so as to fulfill a strong need in the marketplace.

These and other objects of the present invention will become readily apparent upon further review of the following specification.

BRIEF DESCRIPTION OF THE DRAWINGS

FIG. 1 is a chart, which shows a comprehensive grading scale for assessment of rhytides, laxity and photodamage.
FIG. 2 is table for evaluation of skin irritation of a patient using the products of the invention.
FIG. 3 is a table similar to FIG. 2 but evaluating crow's feet, fine lines/wrinkles of a patient using the products of the invention.

DETAILED DESCRIPTION OF THE INVENTION

The present invention pertains to a safe and effective topical skin rejuvenation cream and lotion compositions, which are designed to moisturize and aid in repair of aging skin in multiple and various categories of skin aging. The skin cream and lotion compositions are also beneficial for normal skin to prevent dryness and the effects of aging. The compositions of the current invention encompass a variety of anti-aging active substances that systematically target the various categories of skin aging, including the novel ingredient *Ilex paraguensis* extract. The compositions of the current invention have both moisturizing and anti-aging effects, including but not limited to reducing the appearance of wrinkles, redness and abnormal pigment or brown spots. In addition, the exceedingly high level of redness reduction, and acne and rosacea reduction in skin after use is an unexpected result of this cream composition.

Skin aging may be categorized as intrinsic (or genetic) and extrinsic (or largely sun-induced photoaging). The former category of skin aging manifests as increased skin laxity. The latter category or photoaging typically manifests as wrinkles (rhytids), redness (vascularity or broken blood vessels), brown spots (dyspigmentation), yellowing (solar elastosis), abnormal skin lesions (keratoses), and poor texture. Anti-aging ingredients have been demonstrated to have clinical safety and efficacy in the various categories of skin aging as defined herein. These anti-aging ingredients (defined as "actives") may be classified according to the aging categories they address. The categories of actives that have demonstrated safety and efficacy in the aforementioned comprehensive categories of skin aging are herein defined to include: DNA repair, cellular repair, anti-wrinkle, anti-redness, anti-pigment, anti-UV damage, barrier repair, emollient/moisturizer, anti-abnormal skin lesions, and UV damage reversal.

As has been briefly mentioned, the inventor of the presently described invention has previously recognized various categories of skin aging and photodamage, which categories have been defined and published by the inventor. See, "Rhytides, Laxity, and Photoaging Treated With a Combination Of Radiofrequency, Diode Laser, and Pulsed Light and Assessed With a Comprehensive Grading Scale," Macrene Alexiades-Armenakas MD PhD, Journal of Drugs in Dermatology, September 2006, Volume 5, Issue 8, pages 731-738. In that study, several classes of nonablative laser and light technologies were developed and used to target laxity, rhytides and the various aspects of photoaging. A comprehensive grading scale, developed by the inventor, was used to evaluate the multiple categories of the aging skin and quantitative analysis of changes in each category, as well as overall improvement and patient satisfaction, were calculated.

FIG. 1 of the drawings shows the inventor's Comprehensive Grading Scale For Assessment of Rhytides, Laxity and Photodamage, which plots the various categories of skin aging and photodamage versus a 0 to 4 grading scale. The inventor's previous study used the Comprehensive Grading Scale shown in FIG. 1 to assess the efficacy of several classes of nonablative laser and light technologies, i.e., infrared laser, intense pulsed light and radiofrequency energy, in targeting the various classes of skin aging and photodamage.

The present multi-active microtargeted anti-aging skin cream composition of the invention and the skin cream polymer technology of the invention, extends the use of the Comprehensive Grading Scale and treatment protocol used with the non-ablative laser and light technologies to the field of cosmetic creams and lotions. The present invention, for the first time, targets a specific list of ingredients, which specifically and comprehensively address the aforementioned anti-aging categories in a single cosmetic product. The present invention provides an anti-aging agent and skin cosmetic composition having a high number and variety of active substances ("actives"), including novel substances, and excellent safety and efficacy in all of the various defined categories of skin aging, including but not limited to, wrinkles, abnormal pigment or brown spots due to aging of the skin and an unexpectedly high efficacy in the reduction of redness.

The present invention microencapsulates each ingredient in an appropriate liposomal delivery system where appropriate for precise inter- or intra-cellular delivery to the intended cell targets in the skin. Numerous ingredients are microencapsulated such that they are protected from surrounding ingredients and penetrate to desired strata within the skin. Lipid spheres that contain an aqueous core are called liposomes, from the Greek for "fat body". Liposomes are different from micelles structurally in that they have a bilayer membrane. In the human body, natural liposomes, like micelles, are composed of lecithin phospholipids. Liposomes differ from micelles also in that they are generally larger and have the advantage of being able to carry both fat-soluble and water-soluble contents.

There are a large variety and types of liposomes that may be selected and designed based on a number of properties, one important one ultimately being the ability to target various levels of the epidermis and dermis. For example, non-hydrogenated soy lecithin liposomes have been shown to target epidermis, without significant transport to deeper layers. The anti-aging ingredients which were intended to target the epidermis, such as antioxidants including vitamins C, E and ferulic acid, were therefore prepared in such liposomal delivery systems. In contrast, other types of liposomes such as hydrogenated soy lecithin liposomes under 200 nm in size, have been shown to achieve appreciable delivery to the deeper layers, and were especially chosen to deliver the ingredients intended for action in deeper layers, such as those which play a role in collagen synthesis. The liposomes selected for the basal layer epidermal targeting of DNA repair, UV repair and antioxidant ingredients include such compositions as phosphatidyl ethanolamine, phosphatidyl choline, oleic acid and cholesteryl hemisuccinate, which have been shown to result in basal cell layer delivery. This targeting would be selected for the ingredients intended to reverse mutations accrued in the basal layer of the epidermis. Cationic liposomes were selected in order to augment intracellular delivery of antioxidants, such as vitamins C and E. In order to increase penetration between cells of the stratum corneum and ultimately into the dermis, specifically liposomes with an edge activator, such as a single-chain surfactant an example being sodium deoxycholate, may be chosen. This increases the deformability of the liposome facilitating entry and would be chosen specifically for ingredients targeting within the epidermis or the dermis. In the current invention, the aforementioned characteristics that determine level of penetration and intracellular targeting were precisely selected according to the type of anti-aging ingredient such that each ingredient was delivered to the intended target cells.

A preferred version of the skin care cream of the invention will now be described. However, it should be understood that various changes and modifications may be possible and the invention is not limited to any one specific embodiment.

In one preferred form, the skin rejuvenation cream and lotion compositions of the invention contain, an advanced cream polymer base. The cream polymer base component preferably has the following ingredients deionized water, stearic acid, cetyl alcohol, hydrogenated lecithin, sodium methyl stearoyl taurate and squalane. The multi-active anti-aging skin rejuvenation cream and lotion composition can also contain glycerin, dimethicone, xantham gum, disodium EDTA, and sorbitan stearate.

The preferred formulations of the invention also contain *Tremella fuciformis* extract (preferably Tremoist-TP brand);

*Helianthus annus* (sunflower) seed extract (preferably Soline brand); and *Santalum album* (sandalwood) extract (preferably Bois II brand).

The DNA repair ingredients include acetyl tyrosine, proline, and adenosine triphosphate and hydrolyzed vegetable protein (preferably Unirepair T-43 brand); or t-4 endonuclease (preferably AGI Dermatics brand); or *Micrococcus* lysate and Plankton and Blue Algae Extracts (Barnet brand).

The amino acid ingredients include arginine, aspartic acid, glycine, alanine, serine, valine, proline, threonine, isoleucine, histidine, and phenylalanine (preferably Prodew 500 brand) or glucosamine.

The hyaluronic acid ingredient includes sodium hyaluronate in small molecular weight (preferably HyActive brand).

The liposomes and nanovesicles include *Arabidopsis thaliana* extract, lecithin, laurdimonium hydroxypropyl hydrolyzed soy protein, hydroxyethylcellulose and preferably Roxisomes, Ultrasomes, Oxisomes and Photosomes from Barnet brands and Cytovector Ferulic from BASF brand.

The vitamin C derivative ingredient includes tetrahexyldecyl ascorbate (preferably BV-OSC brand) or magnesium ascorbyl phosphate.

The ergothioneine ingredient is included (preferably Thiotaine, AGI Dermatics).

The microencapsulated ferulic acid ingredient includes ferulic acid, laurdimonium hydroxypropyl hydrolyzed soy protein, and hydroxyethylcellulose (preferably the Cytovector. Ferulic, BASF brand).

The *Ilex* genus is a member of the holly family, Aquifoliaceae, and is found worldwide in subtropical and tropical regions of both hemispheres. The *Coffea arabica, Ilex paraguensis, Theobroma cacao* and *Chrysanthemum parthenium* extracts are USDA-certified organically grown (preferably the Vege Tech brands).

The resveratrol ingredient may be obtained from a variety of sources, preferably the DKSH or Herb-X brands.

The acetyl tetrapeptide ingredient is the Thymulen-4 (Uniplex brand): palmitoyl oligopeptide and palmitoyl tetrapeptide-7 ingredients may be used (preferably Matxixyl brand).

Bisabolol ingredient is available from a variety of sources, preferably the Lipo and Symrise brands or the Bisabolol-Natural by Kinetik Technologies).

The caffeine ingredients may be obtained from a variety of sources, preferably the BASF brand.

The dimethicone ingredient may be obtained from a variety of sources, preferably the Botanisil DM-93 brand.

For each ounce of the cream base component, the preferred formulations contain:
between about 0.50 and 2.00% of the ergothioneine;
between about 0.10 and 2.00% of the resveratrol;
between about 0.01 and 5.00% of the acetyl tetrapeptide-2 or other active peptide;
between about 0.50 and 4.00% of ferulic acid;
between about 0.10 and 3.00% of the *Coffea Arabica* seed extract;
between about 0.10 and 2.00% of the *Ilex Paraguariensis* Leaf extract; and/or alternatively or in addition to *Camellia sinensis* extract
between about 0.10 and 2.00% of the *Chrysanthemum Parthenium* extract;
between about 0.10 and 1.00% of the caffeine;
between about 0.10 and 1.00% of the bisabolol;
between about 0.10 and 2.00% of the *Tremella fuciformis* extract;
between about 0.10 and 2.00% of the tetrahexyldecyl ascorbate or Vitamin C derivative;
between about 0.01 and 1.00% of the magnesium ascorbyl phosphate;
between about 0.01 and 0.50% tocopherol or Vitamin E derivative;
between about 0.10 and 2.00% sodium hyaluronate between 10 and 200 kDa;
between about 0.01 and 1.00% of arginine;
between about 0.01 and 1.00% of aspartic acid;
between about 0.01 and 1.00% of glycine;
between about 0.01 and 1.00% of alanine;
between about 0.01 and 1.00% of serine;
between about 0.01 and 1.00% of valine;
between about 0.01 and 1.00% of proline;
between about 0.01 and 1.00% of threonine;
Between about 0.01 and 1.00% of isoleucine;
between about 0.01 and 1.00% of histidine;
between about 0.01 and 1.00% of phenylalanine; and/or other amino acid or amino acid derivative;
between about 0.01 and 1.00% of acetyl tyrosine;
between about 0.01 and 3.00% of squalane;
between about 0.50 and 2.00% vegetable protein;
between about 0.01 and 1.00% *Arabidopsis thaliana* extract;
between about 0.01 and 5.00% of adenosine triphosphate;
between about 0.10 and 2.00% lecithin;
between about 0.10 and 3.00% *Philodendron amurense* extract; or alternatively phloretin;
between about 0.10 and 5.00% *Santalum album* extract;
between about 0.10 and 5.00% *Hordeum distichon* extract;
between about 0.50 and 7.00% glycerin;
between about 0.50 and 10.00% dimethicone;
between about 0.10 and 3.00% soy protein;
between about 0.01 and 5.00% of sodium lactate;
between about 0.10 and 5.00% *Helianthus annus* (sunflower) seed extract;

For each ounce of cream base, the compositions of the invention may also optionally contain:
between about 0.01 and 5.00% of palmitoyl pentapeptide or other comparable oligopeptide;
between about 0.10 and 2.00% of the *Camellia sinensis* extract;
between about 0.01 and 1.00% of argeirilline;
between about 0.10 and 3.00% phloretin;
between about 0.10 and 2.00% ubiquinone;
between about 0.05 and 2.00% ascorbyl glucoside;
between about 0.01 and 2.00% green tea polyphenols or purified polyphenolic (−)-epigallocatechin (EGCG);
between about 0.01 and 1.00% T4 endonuclease;
between about 0.01 and 5.00% plankton extract.

The preferred formulations of the invention may also optionally contain:
between about 0.01 and 5.00% Anacystis Nidulans—Liposome delivery of the repair enzyme photolyase sourced from plankton that can absorb and assist in reversing the effects of UV induced skin damage;
between about 0.01 and 5.00% liposomally-encapsulated T4 endonuclease V;
between about 0.01 and 5.00% *Micrococcus luteus* extract;
between about 0.01 and 5.00% glucosamine or other amino acid derivative;
between about 0.01 and 5.00% arbutin;
between about 1.00 and 5.00% *Hordeum distichon* or other barley extracts containing natural EGF-like molecules;
between about 1.00 and 5.00% each of *Simmondsia Chinensis* (Jojoba) Butter, *Theobroma Cacao* (Cocoa) Seed Butter and Hydrogenated Coco Glycerides.

The following examples are preferred embodiments of the multi-active anti-aging skin rejuvenation cream or lotion compositions of the current invention. It is to be noted, however, that these examples are by no means limitations of the invention and that various modifications, and improvements in the manufacturing process, all fall under the scope of this invention.

EXAMPLES

Production Example 1

Cream

Multi-Active Anti-Aging Cream Base. For making the cream polymer base, combine in a beaker the hydrogenated lecithin, sodium methyl stearoyl taurate, glycerin and squalane with hydroxypropylmethylcellulose stearoxy ether. Homogenize. To this, add the phenoxyethanol, caprylyl glycol, ethylhexylglycerine, hexylene glycol, water, xantham gum, Tremella fuciformis polysaccharide, glycerin, disodium EDTA, and caffeine. At this point, homogenize for 10 minutes then mix and begin heating to 80 degrees C. The next step is to mix sorbitan stearate, cetyl alcohol, Helianthus annus seed oil unsapofiniables, Santalum album extract, Philodendron amurense bark extract, Hordeum distichon extract, trimethylopropane tricaprylate/tricaprate, dimethicone, tetrahexyldecyl ascorbate and stearic acid. Cool to 25 degrees C.

The next step involves the addition of the DNA repair actives and amino acids. Acetyl tyrosine, proline, hydrolyzed vegetable protein, adenosine triphosphate are added followed or in conjunction with sodium PCA, sodium lactate, arginine, aspartic acid, PCA, glycine, alanine, serine, valine, proline, threonine, isoleucine, histidine, phenylalanine and water.

The following step is the micro- or liposomal encapsulation of ergothioneine and the Arabidopsis thaliana extract. The ergothioneine and other active ingredients were microencapsulated into liposomes composed of magnesium ascorbyl phosphate, tocopherol, lecithin and water.

The next step is the addition of resveratrol and acetyl tetrapeptide-2 to this liposome-containing mixture. To this is added the previously liposomally-encapsulated ferulic acid preparation containing ferulic acid, lecithin, laurdimonium hydroxypropyl hydrolyzed soy protein and hydroxyethylcellulose.

The organic plant extracts are added in the next successive step as Coffea arabica, Ilex paraguensis, Theobroma cacao and Chrysanthemum parthenum extracts in alcohol. Then final step of the preferred method is the addition of sodium hydroxide to a final pH of 6.8-7.2.

Production Example 2

Cream

Multi-Active Anti-Aging Cream (Base) with the following alteration replace acetyl tetrapeptide-2 with palmitoyl oligopeptide and palmitoyl tetrapeptide-7.

The preferred method of making the skin rejuvenation cream of Example 2 is the same as in Example 1. This cream works particularly well for very wrinkled skin.

Production Example 3

Cream

Multi-Active Anti-Aging Cream (Base) with the following alteration: addition of Camellia sinensis extract.

The preferred method of making the skin rejuvenation cream of Example 3 is the same as in Example 1. This cream works particularly well for very inflamed, sensitive skin and skin with abnormal lesions.

Production Example 4

Cream

Multi-Active Anti-Aging Cream (Base) with the following alteration: addition of glucosamine.

The preferred method of making the skin rejuvenation cream of Example 4 is the same as in Example 1. This cream works particularly well for skin with brown discolorations.

Production Example 5

Lotion

Multi-Active Anti-Aging Cream of example 1 (120 ml) with glycerin 2 tbsp. (1 ounce or 30 ml) water 6 tbsp. (3 oz. or 90 ml).

A preferred method of making the skin rejuvenation cream of Example 5 involves combining the skin rejuvenation cream composition of Example 1 with glycerin and water in a stainless steel receptacle. The combination is then heated to about 37 C and mixed until creamy.

Production Example 6

Cream

Multi-Active Anti-Aging Cream (Base) with the following alteration: addition of ubiquinone.

The preferred method of making the skin rejuvenation cream of Example 6 is the same as in Example 1. This cream works particularly well for skin with solar elastosis.

Production Example 7

Cream

Multi-Active Anti-Aging Cream (Base) with the following alteration, addition of Micrococcus luteus extracted T4 endonuclease and Plankton and Blue Algae Extracts.

The preferred method of making the skin rejuvenation cream of Example 7 is the same as in Example 1. This cream works particularly well for skin with solar elastosis, abnormal skin lesions, or sun-induced discolorations or textural changes and for DNA repair of UV-induced skin damage.

Production Example 8

Cream

Multi-Active Anti-Aging Cream (Base) with the following alteration: addition of Anacystis nidulans extract or phytolase, liposomally-encapsulated.

The preferred method of making the skin rejuvenation cream of Example 8 is the same as in Example 1. This cream works particularly well for skin with solar elastosis, abnormal skin lesions, or UV-induced discolorations or textural changes.

Production Example 9

Cream

Multi-Active Anti-Aging Cream (Base) with the following alteration: addition of Hordeum barley extracts, with natural EGF-like molecules.

The preferred method of making the skin rejuvenation cream of Example is the same as in Example 1. This cream works particularly well for skin with acne or rosacea.

Production Example 10

Cream

Multi-Active Anti-Aging Cream (Base) with the following alteration: addition of *Simmondsia Chinensis* (Jojoba) Butter, *Theobroma Cacao* (Cocoa) Seed Butter and Hydrogenated Coco Glycerides.

The preferred method of making the skin rejuvenation cream of Example 8 is the same as in Example 1. This cream works particularly well for dry or mature skin types, while not interfering with the penetration of actives. This cream also is notable for its extra rich formulation while not exacerbating acne.

Formulation Procedure:
1. in a suitable beaker, combine Sequence #6 ingredients and set aside.
2. In main beaker, combine Sequence #1 ingredients and homogenize until smooth.
3. Add Sequence #2 ingredients and continue to homogenize for approximately 10 minutes. Switch to propeller mixing and begin heating to 80° C.
4. in another beaker, combine Sequence #3 ingredients and heat to 78° C. Mix.
5. When batch temperature reaches 78° C. add Sequence #3 to Sequences #1 and #2 and mix for approximately 15 minutes.

PREFERRED FORMULATION FOR MOST SKIN TYPES

| SEQ. | PERCENT | INGREDIENT | INCI NAME |
|---|---|---|---|
| 1 | 32.50 | Deionized Water | Water |
| 1 | 2 | Net LH | Hydrogenated Lecithin (and) Sodium Methyl Stearoyl Taurate (and) Glycerin (and) Squalane (and) Hydroxypropylmethylcellulose Stearoxy Ether |
| 2 | 0.5 | Botanistat PF-64 | Phenoxyethanol (and) Caprylyl Glycol (and) Ethylhexylglycerin (and) Hexylene Glycol |
| 2 | 4.00 | Keltrol (1%) | Water (and) Xanthan Gum |
| 2 | .50 | Tremoist-TP | *Tremella Fuciformis* Polysaccharide |
| 2 | 4.00 | Glycerin | Glycerin |
| 2 | 0.10 | Dissolvene Na2 | Disodium EDTA |
| 2 | 0.20 | Caffeine | Caffeine |
| 3 | 0.20 | Bisabolol | Bisabolol |
| 3 | 1.00 | SS-10V | Sorbitan Stearate |
| 3 | 2.00 | Lipocol C | Cetyl Alcohol |
| 3 | 4.00 | Soline | *Helianthus Annuus* (Sunflower) Seed Oil Unsaponifiables |
| 3 | 1.00 | Bois II | *Santalum Album* (Sandalwood) Extract (and) *Phellodendron Amurense* Bark Extract (and) *Hordeum Distichon* (Barley) Extract |
| 3. | 2.00 | Lexfeel 21 | Trimethylolpropane Tricaprylate/Tricaprate |
| 3 | 8.00 | Botanisil DM-93 | Dimethicone |
| 3 | .50 | BV-OSC | Tetrahexyldecyl Ascorbate |
| 3 | 1.00 | Lipo Stearic Acid | Stearic Acid |
| 3 | 1.00 | Organic Cocoa Butter VTFO-R01022.116SU | *Helianthus Annuus* (Sunflower) Seed Oil (and) *Theobroma Cacao* (Cocoa) Seed Butter |
| 4 | 7.00 | Prodew 500 | Sodium PCA (and) Sodium Lactate (and) Arginine (and) Aspartic Acid (and) PCA (and) Glycine (and) Alanine (and) Serine (and) Valine (and) Proline (and) Threonine (and) Isoleucine (and) Histidine (and) Phenylalanine (and) Water |
| 4. | 4.00 | Unirepair T-43 | Butylene Glycol (and) Acetyl Tyrosine (and) Proline (and)Hydrolyzed Vegetable Protein (and)Adenosine Triphosphate |
| 5 | 5.00 | Deionized Water | Water |
| 5 | 1.00 | HyActive | Sodium Hyaluronate |
| 6 | 3.00 | Roxisomes | *Arabidopsis Thaliana* Extract (and) Lecithin (and) Water |
| 6 | 3.00 | Oxysomes | Magnesium ascorbyl Phosphate (and) Tocopherol (and) Lecithin (and) Water |
| 6 | 2.00 | Thiotaine | Ergothioneine |
| 7 | .50 | HerbEx Resveratrol 0.5 | Resveratrol |
| 7 | 4.00 | Thylumen-4 | Water (and) Dextran (and) Acetyl Tetrapeptide-2 |
| 7 | 3.00 | Cytovector Ferulic | Water (and) Butylene Glycol (and) Lecithin (and) Ferulic Acid (and) Laurdimonium Hydroxypropyl Hydrolyzed Soy Protein (and) Hydroxyethylcellulose |
| 7 | 1.00 | Organic Green Coffee Bean Extract VTFO-1019.145GA | Water (and) *Coffee Arabica* (Coffee) Seed Extract (and) Alcohol |
| 7 | 1.00 | Organic Yerba Mate Extract VTFO-1076.145GA | Water (and) *Ilex Paraguariensis* Leaf Extract (and) Alcohol |
| 7 | 1.00 | Organic Feverfew Extract VTFO-0620.145GA | Water (and) *Chrysanthemum Parthenium* (Feverfew) Extract (and) Alcohol |
| 8 | qs | NaOH (18%) | Water (and) Sodium Hydroxide |

6. Switch to propeller mixing, and cool to 25° C.
7. At 25° C., add Sequence #4 ingredients.
8. Combine Sequence #5 ingredients and mix until a clear gel is obtained.
9. Slowly add Sequence #5 then #6 to the batch and mix.
11. Add Sequence #7.
12. Adjust the batch to pH 7.00-8.00 with Sequence #8.

The formulation procedure for the Extra Rich Base product is the same as for the Preferred Formulation for Most Skin Types previously described.

Clinical Efficacy Study

A clinical efficacy study was conducted with 31 female subjects to determine if Test Article: Dr. Macrene 37 Extreme Actives used twice daily for 8 weeks helped to improve the

PREFERRED FORMULATION WITH EXTRA RICH BASE

| SEQ. | PERCENT | INGREDIENT | INCI NAME |
|---|---|---|---|
| 1 | 38 | Deionized Water | Water |
| 1 | 2 | Net LH | Hydrogenated Lecithin (and) Sodium Methyl Stearoyl Taurate (and) Glycerin (and) Squalane (and) Hydroxypropylmethylcellulose Stearoxy Ether |
| 2 | 1.00 | Botanistat PF-64 | Phenoxyethanol (and) Caprylyl Glycol (and) Ethylhexylglycerin (and) Hexylene Glycol |
| 2 | 1.00 | Tremoist TP | *Tramella Fuciformis* Polysaccharide |
| 2 | 2.00 | Glycerin | Glycerin |
| 2 | 0.10 | Dissolvene Na2 | Disodium EDTA |
| 2 | 0.10 | Caffeine | Caffeine |
| 3 | 3.00 | Isojojoba-35 | *Simmonondsia Chinensis* (Jojoba) Butter |
| 3 | 0.10 | Bisabolol | Bisabotol |
| 3 | 0.20 | SS-10V | Sorbitan Stearate |
| 3 | 2.00 | Soline | *Helianthus Annuus* (Sunflower) Seed Oil Unsaponifiables |
| 3 | 1.00 | Bois II | *Santalum Album* (Sandalwood) Extract (and) *Phellodendron Amurense* Bark Extract (and) *Hordeum Distichon* (Barley) Extract |
| 3 | 2.00 | Organic Cocoa Butter | *Theobroma Cacao* (Cocoa) Seed Butter |
| 3 | 6.00 | Dow Corning 200 Fluid, 350 cs. | Dimethicone |
| 3 | 1.00 | BV-OSC | Tetrahexyldeeyl Ascorbate |
| 3 | 2.00 | Lipo Stearic Acid | Stearic Acid |
| 3 | 2.00 | Lipocol SC | Cetearyl Alcohol |
| 3 | 2.00 | Softisan 100 | Hydrogenated Coco Glycerides |
| 3 | 0.50 | Organic Cocoa Butter VTFO-R01022.116SU | *Helianthus Annuus* (Sunflower) Seed Oil (and) *Theobroma Cacao* (Cocoa) Seed Butter |
| 4 | 7.00 | Prodew 500 | Sodium PCA (and) Sodium Lactate (and) Arginine (and) Aspartic Acid (and) PCA (and) Glycine (and) Alanine (and) Serine (and) Valine (and) Praline (and) Threonine (and) Isoleucine (and) Histidine (and) Phenylalanine (and) Water |
| 5 | 1.00 | Deionized Water | Water |
| 5 | 1.00 | HyActive | Sodium Hyaluronate |
| 6 | 2.00 | Roxisomes | *Arabidopsis Thaliana* Extract (and) Lecithin (and) Water |
| 6 | 2.00 | Ultrasomes | *Micrococcus Lystae* |
| 6 | 2.00 | Photosomes | Plankton Extract (and) Lecithin |
| 6 | 3.00 | Oxysomes | Magnesium ascorbyl Phosphate (and) Tocopherol (and) Lecithin (and) Water |
| 6 | 1.00 | Thiotaine | Ergothioneine |
| 7 | 1.00 | HerbEx Resveratrol 0.5 | Resveratrol |
| 7 | 5.00 | Matrixyl 3000 | Glycerin (and) Water (and) Butylene Glyeol (and) Carbomer (and) Polysorbate-20 (and) Palmitoyl Oligopeptide (and) Palmitoyl Tetrapeptide-7 |
| 7 | 3.00 | Cytovector Ferulic | Water (and) Butylene Glycol (and) Lecithin (and) Ferulic Acid (and) Laurdimonium Hydroxypropyl Hydrolyzed Soy Protein (and) Hydroxyethylcellulose |
| 7 | 1.50 | Organic Green Coffee Bean Extract VTFO-1019.145GA | Water (and) *Coffee Arabica* (Coffee) Seed Extract (and) Alcohol |
| 7 | 1.00 | Organic Yerba Mate Extract VTFO-1076.145GA | Water (and) *Ilex Paraguariensis* Leaf Extract (and) Alcohol |
| 7 | 0.50 | Organic Feverfew Extract VTFO-0620.145GA | Water (and) *Chrysanthemum Parthenium* (Feverfew) Extract (and) Alcohol |
| 8 | 1.00 | Deionized Water | Water |
| 8 | 2.00 | Glucosamine | Glucosamine |
| 9 | qs | NaOH (18%) | Water (and) Sodium Hydroxide | appearance of crow's feet fine lines/wrinkles, brown skin blotches and red skin blotches. The study was conducted during the spring months (April-June) when environmental exposure to sunlight/UV radiation would be at high levels. Even though study participants limited their sunlight exposure and were provided SPF, ordinary and inadvertent exposure to UV radiation would be expected during the study period. Given this heightened potential sun exposure, the changes observed are considered to represent a dramatic improvement from baseline.

Crow's Feet Fine Lines/Wrinkles were significantly (p≦00.1) improved after 4, 6 and 8 weeks of product use with up to 77% of the subjects showing improvement at 6 weeks.

Red/Blotchy Skin was significantly improved after 4, 6, and 8 weeks of product use, with up to 87% of the subjects showing improvements at 8 weeks.

Brown/Blotchy Skin was significantly improved after 8 weeks of product use, with up to 74% of the subjects showing improvement.

No skin irritation was observed during the study duration on any subject.

Safety Test
Irritation Evaluation

Thirty-one female subjects between the ages of 35 and 64 were enrolled in safety evaluation of the invention. Subjects were provided with two 1-ounce jars of the multi-active anti-aging cream and instructed to apply a small aliquot of the cream to the facial skin twice daily over an 8-week study duration. Subjects were given a daily diary to record product use and to record the date of any changes or irritation to the skin. Subjects were evaluated at baseline, 4-week, 6-week, and 8-week intervals (see FIG. 2 of the drawings). At each evaluation, a trained technician evaluated the face of each subject for irritation. This evaluation was for safety purposes only and was not used in determining efficacy. Scale for scoring irritation was as follows: 0=no irritation present, +=barely perceptible irritation present, 1=mild irritation present, 2=moderate irritation present, 3=marked irritation present, 4=severe irritation present (FIG. 2). No skin irritation was observed during the 8-week study duration in any subject. The 0 irritation in the entire study pool at every timepoint demonstrates the extraordinary level of safety achieved by the current invention, owing to the selection of ingredients with a high safety profile and the omission of potential irritants as aforementioned in the description of the invention.

According to the results of these tests, the multi-active anti-aging cream was determined to clearly demonstrate a high degree of safety. No irritation was noted in any patient, showing extraordinarily high level of safety with the invention.

Wrinkle Reduction Test of Multi-Active Anti-Aging Cream

Thirty-one female subjects between the ages of 35 and 64 were enrolled in safety evaluation of the invention. Subjects were provided with two 1-ounce jars of the multi-active anti-aging cream and instructed to apply a small aliquot of the cream to the facial skin twice daily over the 8-week study duration. Subjects were given a daily diary to record product use and to record the date of any changes or irritation to the skin. Subjects were evaluated at baseline, 4-week, 6-week and 8-week intervals. At all visits, a trained technician evaluated the appearance of crow's feet fine lines/wrinkles on the face of subject according to the following scale:

Scale for Scoring Crow's Feet Fine Lines/Wrinkles
0=None
1-3=Slight
4-6=Noticeable
7-9=Very Noticeable At each visit, a trained technician evaluated fine lines/wrinkles at the crow's feet area of each subject. Individual score and statistical analyses are presented in FIG. 3.

The following table presents a summary of mean crow's feet fine/line wrinkle scores.

TABLE I

Wrinkle reduction following application of multi-active anti-aging skin cream.
Mean (+Standard Deviation [S.D])
Crow's Feet Fine Line/Wrinkle Scores and
% Change from Baseline

| | Mean Score ± S.D. | p-Value | Change from Baseline |
|---|---|---|---|
| Baseline | 5.9 ± 0.7 | | |
| 4 Weeks | 5.4* ± 0.6 | <0.001 | −8.5% |
| 6 Weeks | 4.9* ± 0.6 | 0.001 | −17.-% |
| 8 Weeks | 4.9* ± 0.7 | 0.001 | −17.-% |

*Statistically significant difference from baseline (p ≦ 0.05).

When measurements taken after 4, 6 and 8 weeks of product use were compared with baseline measurements, there was:
 an 8.5% decrease (improvement) in the appearance of crows feet fine lines/wrinkles after 4 weeks of product use;
 a 17.0% decrease (improvement) in the appearance of crow's feet fine lines/wrinkles after 6 weeks of product use; and
 a 17.0% decrease (improvement) in the appearance of crow's feet fine lines/wrinkles after 8 weeks of product use.

The improvements observer after 4, 6 and 8 weeks of products use were highly significant (p<0.001) when compared with baseline.

Redness Reducing Test of Multi-Active Anti-Aging Cream

Thirty-one female subjects between the ages of 35 and 64 were enrolled in safety evaluation of the invention. Subjects were provided with two 1-ounce jars of the multi-active anti-aging cream and instructed to apply a small aliquot of the cream to the facial skin twice daily over the 8-week study duration. Subjects were evaluated at baseline, 4-week, 6-week and 8-week intervals using an objective, computer-based analysis with the Visia CR® advanced clinical digital evaluation technology. At all visits, digital images of the face of each subject were taken using the Visia CR® Imaging System. Digital images were token from the front, right and left views. In order to ensure consistency between the photographs, each subject was draped with a black cloth around the shoulders to eliminate the appearance of clothing in the pictures and each subject wore a black headband to pull hair off and away from the face. The images were analyzed using Image Pro® software to determine changes in red blotchy skin.

In order to determine any changes in red/blotchy skin, the CIE a* value was analyzed. The a* value measures redness/erythema in the skin (Alexiades-Armenakas et al Arch Dermatol 2003). A decrease in the a* value corresponded to an improvement (less red/blotchy) effect and an increase in the a* value represented a worsening (more red/blotchy effect) (Alexiades-Armenakas et al 2003).

At each visit, a trained technician took digital images of the face of each subject with the Visia CR®. Using ImpagePro® Software, the images were analyzed to determine changes in red blotchy skin.

TABLE II

Summary of the Visia © red blotchy skin analysis.
Visia CR © Red Blotchy Analysis (a* Value)
Mean (±S.D.) Scores and % Change from Baseline

|  | Mean Score ± S.D. | p-Value | Change from Baseline |
|---|---|---|---|
| Baseline | 9.51 + 1.97 | | |
| 4 Weeks | 9.06 + 1.94 | 0.007 | −4.7 |
| 6 Weeks | 8.90* + 1.46 | 0.001 | −6.4% |
| 8 Weeks | 8.47* + 1.06 | <0.001 | −10.9% |

*Statistically significant difference from baseline (p ≦ 0.05).

When measurements taken after 4, 6 and 8 weeks of product use were compared with baseline images, there was:

an 4.7% decrease (improvement) in the appearance of red blotchy skin after 4 weeks of product use;

a 6.4% decrease (improvement) in the appearance of red blotchy skin after 6 weeks of product use; and a 10.9% decrease (improvement) in the appearance of red blotchy skin after 8 weeks of product use.

The improvements observed at all-time points were statistically significant when compared with baseline.

The exceptionally high degree of improvement in the a* value or red/blotchy effect of the skin observed following application of the multi-active anti-aging cream, the invention, is an unexpected finding. While a large number and variety of plant-derived polyphenols are included in the current invention and such actives have been reported to improve redness, such a large improvement in such a short duration of time (8 weeks) is an unexpected result of the invention.

Reduction of Abnormal Pigment or Brown Spots Test of Multi-Active Multi-Aging Cream Thirty-one female subjects between the ages of 35 and 64 were enrolled in safety evaluation of the invention. Subjects were provided with two 1-ounce jars of the multi-active anti-aging cream and instructed to apply a small aliquot of the cream to the facial skin twice daily over the 8-week study duration. Subjects were evaluated at baseline, 4-week, 6-week and 8-week intervals using an objective, computer-based analysis with the Visia CR® advanced clinical digital evaluation technology. At all visits, digital images of the face of each subject were taken using the Visia CR® Imaging System. Digital images were taken from the front, right and left views. In order to ensure consistency between the photographs, each subject was draped with a black cloth around the shoulders to eliminate the appearance of clothing in the pictures and each subject wore a black headband to pull hair off and away from the face. The images were analyzed using Image Pro® software to determine changes in brown blotchy skin.

In order to determine any changes in brown/blotchy skin, chroma was analyzed. The degree to which a color is free from being mixed with other colors is a good indication of its chromaticity. An increase in the chroma score represented an improvement in skin clarity (less brown/blotchy effect). A decrease represented a worsening (more brown/blotchy effect).

At each visit, a trained technician took digital images of the face of each subject with the Visia CR®. Using ImagePro® Software, the images were analyzed to determine changes in brown blotchy skin. T

TABLE III

Summary of the Visia © brown blotchy skin analysis.
Visia CR © Brown Blotchy Analysis (Chroma)
Mean (±S.D.) Scores and % Change from Baseline

|  | Mean Score ± S.D. | p-Value | Change from Baseline |
|---|---|---|---|
| Baseline | 14.62 + 1.68 | | |
| 4 Weeks | 14.78 + 1.61 | 0.774 | 1.1% |
| 6 Weeks | 14.92 + 1.51 | 0.297 | 2.1% |
| 8 Weeks | 15.12* + 1.62 | 0.046 | 3.4% |

*Statistically significant difference from baseline (p ≦ 0.05).

When measurements taken after 4, 6 and 8 weeks of product use were compared with baseline images, there was:

a 1.1% improvement in brown blotchy skin after 4 weeks of product use;

a 2.1% improvement in brown blotchy skin after 6 weeks of product use and a 3.4% improvement in brown blotchy skin after 8 weeks of product use.

The improvements observed at 8 weeks of product use was statistically significant when compared with baseline.

Reduction of Acneiform Lesions, Rosacea Blemishes or Discolorations

Thirty-one female subjects between the ages of 35 and 64 were enrolled in safety evaluation of the invention. Subjects were provided with two 1-ounce jars of the multi-active anti-aging cream and instructed to apply a small aliquot of the cream to the facial skin twice daily over the 8-week, study duration. Subjects were evaluated at baseline, 4-week, 6-week and 8-week intervals using an objective, computer-based analysis with the Visia CR® advanced clinical digital evaluation technology. At all visits, digital images of the face of each subject were taken using the Visia CR® Imaging System. Digital images were taken from the front, right and left views. In order to ensure consistency between the photographs, each subject was draped with a black cloth around the shoulders to eliminate the appearance of clothing in the pictures and each subject wore a black headband to pull hair off and away from the face. The images were analyzed using Image Pro® software to determine changes in the number of acneiform lesions, rosacea blemishes or discolorations. The number of acneiform lesions decreased by 22.5% at 4 weeks; 29.9% at 6 weeks and 34.5% at 8 weeks of use. The improvements at each timepoint were statistically significant when compared to baseline.

An invention has been provided with several advantages. The present invention is a unique and comprehensive skin cosmetic composition combining and micro-targeting a wide variety of ingredients selected for their applicability to the various categories of skin aging, including the novel ingredient of *Ilex paraguensis*. The composition of the present invention and its embodiments provides unexpected high efficacy in multiple categories of skin aging, including but not limited to wrinkles, brown discolorations of the skin and particularly redness. The multi-active anti-aging cream maintains efficacy in all these categories, while also maintaining a high degree of safety and the absence of potentially irritating or harmful substances such as parabens, propylene glycol, fragrances, or animal or human-derived ingredients. From the standpoint of anti-aging skin care, this invention may be formulated into a skin cosmetic composition and is extremely useful and unprecedented as an anti-aging skin agent, as it serves as a single product encompassing the various anti-aging categories.

The composition of the present invention has a pleasant feel to the skin. Applied daily, it works well to smooth fine lines and wrinkles, reducing the signs of aging. The composition leaves the skin feeling soft and silky to the touch. The composition moisturizes without causing acne breakouts. The extra rich formulation is able to further moisturize dry skin types without the use of petrolatums or oils, therefore without causing acne breakouts.

It is to be understood that the present invention is not limited to the sole embodiments described above, but encompasses any and all embodiments within the scope of the following claims.

What is claimed is:

1. A skin care composition, comprising:
a combination of comprehensive topical anti-aging ingredients for cosmetic application to the skin including in active form at least the following categories of anti-aging ingredients: DNA repair, cellular repair, anti-wrinkle, anti-redness, anti-pigment, anti-UV damage, anti-oxidant, barrier repair, emollient/moisturizer characteristics, pro-collagen, anti-abnormal skin lesions and UV damage reversal;
wherein the composition includes at least 37 of the following ingredients that are micro-encapsulated:
Dimethicone
Glycerin
*Theobroma Cacao* (Cocoa) Seed Butter
*Helianthus Annuus* (Sunflower) Seed Oil or Extract
*Simmondsia chinensis* (Jojoba) Butter or Extract
Hydrogenated Coco Glycerides
Glucosamine
Resveratrol
Palmitoyl Tetrapeptide-7
Palmitoyl Oligopeptide
Caffeine
Ferulic Acid
Ergothioneine
Magnesium Ascorbyl Phosphate
Sodium Hyaluronate
Tetrahexyldecyl Ascorbate
Tocopherol
Alanine
Arginine
Aspartic Acid
Glycine
Histidine
Isoleucine
PCA (pyrrolidone carboxylic acid)
Phenylalanine
Proline
Serine
Threonine
Valine
*Arabidopsis thaliana* Extract
Bisabolol
*Chrysanthemum parthenium* (Feverfew) Extract
*Coffea Arabica* (Coffee) Seed Extract
*Hordeum distichon* (Barley) Extract
*Ilex paraguariensis* (Yerba Mate Tea) Leaf Extract
*Micrococcus Lysate*
Phellodendron amurense Bark Extract
Plankton and Blue Algae Extract
Santalum album (Sandalwood) Extract
*Theobroma cacao* (Cocoa) Seed Extract
Tremella fuciformis (Mushroom Extract)
Sodium PCA (pyrrolidone carboxylic acid)
Sodium Lactate
Squalane
Soy protein.

2. The skin care composition of claim 1, wherein the anti-aging ingredients in active form are selected based upon the proven safety and efficacy of each ingredient within each anti-aging ingredient category defined in claim 1.

3. The skin care composition of claim 1, wherein the composition of the invention systematically targets individual ingredients within each category of anti-aging ingredients defined in claim 1 to the anatomic location within the skin where they function to yield their intended effect.

4. The skin care composition of claim 1, wherein the DNA repair and UV damage reversal or anti-UV damage ingredients are lipoencapsulated in liposomes consisting of non-hydrogenated soy lecithin in order to target the epidermis.

5. The skin care composition of claim 4, wherein the ingredients that are lipoencapsulated are selected from the group consisting of phosphatidyl ethanolamine, phosphatidyl choline, oleic acid and cholesteryl hemisuccinate.

6. The skin care composition of claim 4, wherein cationic liposomes are selected in order to augment intracellular delivery of the class of ingredients that comprise antioxidants.

7. The skin care composition of claim 1, wherein the anti-wrinkle and cellular repair class of ingredients are comprised of non-hydrogenated soy lecithin liposomes.

8. The skin care composition of claim 1, wherein the anti-redness class of ingredients use hydrogenated soy lecithin liposomes under 200 nm in size together with phosphatidyl ethanolamine, phosphatidyl choline, oleic acid and cholesteryl hemisuccinate.

9. The skin care composition of claim 1, wherein, in order to increase penetration between stratum corneum cells and ultimately into the dermis, liposomes with an edge activator comprising a single-chain surfactant, are chosen for the delivery of barrier repair and emollient/moisturizer classes of ingredients.

10. The skin care composition of claim 9, wherein the single-chain surfactant is sodium deoxycholate.

11. The skin care composition of claim 1, wherein, for the pro-collagen class of anti-aging ingredients hydrogenated soy lecithin liposomes under 200 nm in size are used.

* * * * *